United States Patent
Shigeura et al.

(10) Patent No.: US 7,501,284 B2
(45) Date of Patent: Mar. 10, 2009

(54) APPARATUS AND METHOD FOR SPECIFIC RELEASE OF CAPTURED EXTENSION PRODUCTS

(75) Inventors: John Shigeura, Portola Valley, CA (US); Jer-Kang Chen, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 91 days.

(21) Appl. No.: 09/908,994

(22) Filed: Jul. 17, 2001

(65) Prior Publication Data

US 2002/0076718 A1 Jun. 20, 2002

Related U.S. Application Data

(60) Provisional application No. 60/222,371, filed on Jul. 31, 2000.

(51) Int. Cl.
*G01N 33/00* (2006.01)
*G01N 25/20* (2006.01)
*C12M 1/36* (2006.01)
*C07H 21/04* (2006.01)
*B01L 3/00* (2006.01)

(52) U.S. Cl. ............... 436/94; 435/287.2; 536/23.1; 422/58; 422/59; 422/99

(58) Field of Classification Search ............ 435/6, 435/91.1, 91.2, 183, 287.2; 436/94; 536/23.1, 536/24.3, 24.31, 24.33
See application file for complete search history.

(56) References Cited

U.S. PATENT DOCUMENTS

| | | | |
|---|---|---|---|
| 5,527,670 A | | 6/1996 | Stanley |
| 5,593,838 A | * | 1/1997 | Zanzucchi et al. .............. 435/6 |
| 5,607,646 A | * | 3/1997 | Okano et al. ................. 422/101 |
| 5,849,486 A | * | 12/1998 | Heller et al. .................... 435/6 |
| 5,962,228 A | * | 10/1999 | Brenner .......................... 435/6 |
| 6,124,092 A | * | 9/2000 | O'Neil et al. ................... 435/6 |
| 6,207,818 B1 | * | 3/2001 | Hellyer et al. ............. 536/24.3 |
| 6,419,824 B1 | * | 7/2002 | Gjerde et al. ............. 210/198.2 |

FOREIGN PATENT DOCUMENTS

| | | |
|---|---|---|
| WO | WO 96/02836 | 2/1996 |
| WO | WO 98/14610 | 4/1998 |
| WO | WO 00/31304 | 6/2000 |

OTHER PUBLICATIONS

Search Report from PCT/US01/22789 dated Jul. 19, 2002.
"A System for Multiplex Sequencing and Hybridization-Based Pull-out of DNA Extension Products," *PE Applied Biosystems Product Literature*, pp. 1-10, Jan. 29, 1999.

* cited by examiner

*Primary Examiner*—Bradley L Sisson
(74) *Attorney, Agent, or Firm*—Knobbe Martens Olson & Bear LLP

(57) ABSTRACT

Apparatus and methods for separating different polynucleotide populations in a mixture are provided, wherein different polynucleotides or polynucleotide populations are captured on different solid support. After hybridization, polynucleotides are selectively released from a selected support by altering a physical property of that support. The released polynucleotides can be eluted from a common flow path and isolated.

18 Claims, 5 Drawing Sheets

APPARATUS AND METHOD FOR SPECIFIC RELEASE OF CAPTURED EXTENSION PRODUCTS

CROSS-REFERENCE TO RELATED APPLICATIONS

This application claims priority to provisional application Ser. No. 60/222,371, filed Jul. 31, 2000, which is incorporated herein by reference.

FIELD OF THE INVENTION

The present invention relates to apparatus and methods for separating different polynucleotide populations from each other, wherein polynucleotide capture and elution are performed in a common flow path. The invention also relates to a programmed device and a program of instructions (e.g., software) that is executed by the device for implementing methods of the invention.

INTRODUCTION

Polynucleotide sequencing is an important, well established technique in molecular biology and has become integral to virtually all aspects of molecular genetics. With the undertaking of massive sequencing projects, such as the Human Genome Project, as well as comparative sequencing of known genes for diagnostic purposes, the demand to reduce the time and overhead associated with such sequencing is greatly increasing.

To analyze multiple polynucleotide sequences in a sample, it is desirable to use as few reaction vessels as possible in order to use reagents efficiently and reduce liquid manipulations. For example, DNA sequencing using the Sanger method has been dramatically simplified using dye terminators labeled with base-specific fluorescent dyes for each of the four standard bases (A, C, G and T). This approach has made possible the performance of template-dependent primer extension in a single reaction mixture in the presence of four terminators, followed by sequence analysis of the resulting fragment mixture in a single electrophoretic path. However, this approach has usually required a different sequencing reaction mixture for each different target. One attempt to address this problem was proposed by Church et al. (Science 240:185, 1988; and U.S. Pat. No. 5,149,625), wherein sequencing fragments are produced by different, sequence-specific sequencing primers containing distinct tag sequences to identify extension products from each template-specific primer. After gel electrophoresis, the separated fragments are transferred onto a membrane and iteratively hybridized with different tag-specific probes to serially determine the sequence of each different target, one at a time. Unfortunately, this method is cumbersome to practice and also requires four different extension reaction mixtures per target template, since four different primer tags are required to identify the four possible 3' terminators at the ends of the fragments.

DNA sequencing is but one example of methods that involve mixtures of different polynucleotides. More generally, it is often desirable to simultaneously generate a plurality of polynucleotide populations in a single reaction mixture, followed by isolation of the different populations from the mixture for further analysis or manipulation. Ideally, such a method should be convenient to perform and should allow the isolation and separation of the different polynucleotide populations in analytical or preparative amounts.

SUMMARY OF THE INVENTION

The present invention provides apparatus and methods whereby the separation and isolation of different polynucleotide populations can be achieved using a single flow path.

In one aspect, the invention includes an apparatus for separating one or more different-sequence polynucleotides from a polynucleotide mixture. The apparatus comprises (a) a flow path, (b) a plurality of solid supports which are disposed in series in the flow path, each support having bound thereto a sequence-specific capture agent that is complementary to a different-sequence target that may be present in the polynucleotide mixture. In a preferred, optional embodiment, the apparatus further comprises (c) a control mechanism in communication with the supports for altering a physical property of each support, separately from the other supports, between a target-binding state and a target-nonbinding state. In operating the apparatus, passage of the mixture through the plurality of solid supports is effective to specifically bind different-sequence targets to a complementary capture agent on each support when the supports are each in a target-binding state. Thereafter, a physical property of a first selected support can be altered to a target-non-binding state to release bound polynucleotides from that support. The released polynucleotides can be eluted from that support by passage of a liquid medium (solvent) through the flow path while polynucleotides captured on the other supports remain bound to those supports. Bound polynucleotides on the remaining supports can be released and eluted separately by repetition of the foregoing steps.

In one embodiment, the control mechanism is capable of performing steps (ii) and (iii) simultaneously.

In another embodiment, the physical property is temperature, and the control mechanism comprises a temperature control element for selectively heating a selected support to release polynucleotides from that support. For example, the control mechanism can comprise a plurality of heating elements, one for each support, and may be operable to activate the heating elements to release polynucleotides from one support at a time.

In another embodiment, the physical property is voltage potential, and the control mechanism comprises a voltage control element for setting individual electrical potentials of the solid supports to release polynucleotides from that support.

In another aspect, the invention includes a method for isolating one or more different-sequence polynucleotides from a mixture. In the method, the mixture is flowed through a flow path containing a plurality of solid supports which are located in series in the flow path, each support having bound thereto a sequence-specific capture agent complementary to a different-sequence polynucleotide, under conditions effective to specifically bind different-sequence polynucleotides to corresponding sequence-specific capture agents on one or more of the supports. After binding is complete, bound polynucleotides can be released from a selected support by altering a physical property of that support while leaving unaltered the same physical property of one or more of the other supports. The released polynucleotides are eluted through the flow path such that the eluted polynucleotides can be isolated in separated form.

In one embodiment, (i) the polynucleotide mixture comprises a plurality of different polynucleotide populations, each different polynucleotide population comprising a plurality of different polynucleotides that contain a distinct sequence associated with that population, and (ii) different sequence-specific capture agents on the different solid supports are complementary to different polynucleotide populations in the mixture. An example of such populations is a mixture of sequencing ladders as discussed further below. In another embodiment, the polynucleotide mixture comprises a plurality of PCR products. In yet another embodiment, the polynucleotide mixture comprises a plurality of ligation products.

These and other objects and features of the invention will become more fully apparent when the following detailed description is read in conjunction with the accompanying drawings.

DETAILED DESCRIPTION OF THE INVENTION

I. Definitions

Figure 1:
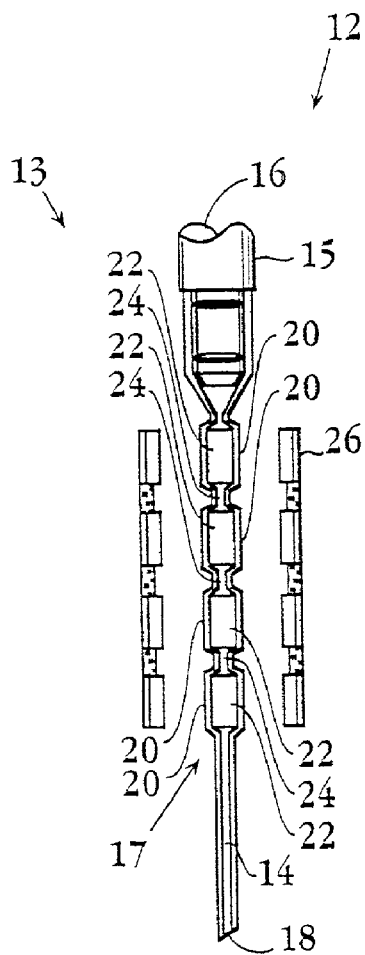
FIG. 1 illustrates a sectional view of a column defining an exemplary flow path in accordance with the invention.

"Oligonucleotide" and "polynucleotides" are used interchangeably herein and are intended to have the same meaning. As used herein, these terms refer to naturally occurring polynucleotides, e.g., DNA or RNA, and analogs thereof. Such analogs include, but are not limited to, phosphoramidates, peptide-nucleic acids, phosphorothioates, methylphosphonates, and the like. In addition to having non-naturally occurring backbones, analogs may also comprise base analogs such as 7-deazaguanosine, 5-methyl cytosine, inosine, and the like. Descriptions of how to synthesize polynucleotides can be found, among other places, in U.S. Pat. Nos. 4,373,071; 4,401,796; 4,415,732; 4,458,066; 4,500,707; 4,668,777; and 4,973,679.

"Recovery tag" as used herein refers to a compound (or portion of a compound) that is a member of a specific binding pair of molecules. A recovery tag may belong to any class of macromolecule, e.g., polynucleotides, carbohydrates, polypeptides, and the like. Alternatively, recovery tags may belong to a class of non-naturally occurring molecules. Preferably, recovery tags are oligonucleotides. When the recovery tag is an oligonucleotide, the recovery tag may comprise none, part, or all of the template-annealing sequence of a recoverable primer. Recovery tags (and their respective recovery tag binding compounds) are selected so as to avoid the binding of the recovery tags at improper locations, e.g., different recovery tag oligonucleotides are preferably non-cross hybridizing.

When the recovery tag is an oligonucleotide, the recovery tag may optionally comprise a "balancing polynucleotide" sequence. "Balancing polynucleotide" refers to polynucleotides that hybridize to the recovery tag binding compound, but do not specifically hybridize to the sequencing (or amplification) template. Balancing polynucleotides are optionally present on recoverable primers. The balancing polynucleotide may be used to equalize, i.e., balance, the melting temperatures of the duplex (or triplex) formed between the different recovery tag and the recovery tag binding compound pairs used together in the same reaction vessel. Similarly, the balancing polynucleotide may be used to equalize, i.e., balance, the melting temperatures of the duplex (or triplex) formed between the different recovery tag and the recovery tag binding compound pairs that are to be denatured under similar conditions.

"Recovery tag binding compound" refers to the member of a specific binding pair that is not the recovery tag on a given recoverable primer. In embodiments of the invention employing polynucleotides as recovery tags, the recovery tag binding compound comprises a polynucleotide sequence that is complementary or partially complementary to the recovery tag polynucleotide of interest. Individual recovery tag binding compound molecules may comprise multiple copies of the complementary (or partially complementary) polynucleotide sequence. Branched polynucleotides, for example as described in published PCT patent application WO 96/016104 and published European patent application EP 646595, may be used to increase the effective concentration of binding sites for recovery tags.

"Recoverable primer" refers to an oligonucleotide primer that comprises a recovery tag. Recoverable primers may be used to specifically prime a polynucleotide sequencing reaction, a polynucleotide amplification reaction, or other primer extension reaction, i.e., recoverable primers comprise a polynucleotide sequence that can specifically bind to a specific (usually predetermined) site on a template for sequencing (or amplification). The portion of the recoverable primer that may site-specifically hybridize to a template is referred to herein as the "template-annealing sequence" of the recoverable primer. The template-annealing sequence is of sufficient length to specifically hybridize to a site or sites on the template of interest, typically 18-36 nucleotides in length. Template-annealing sequences for use in polynucleotide sequencing must hybridize to unique sites on the template of interest. The recovery tag is coupled to the primers in such a way as to avoid having the recovery tag interfere with the ability of the recoverable primer to site-specifically hybridize to the priming site, e.g., the recovery tag may be joined at, or proximal to, the 5' end of the recoverable primer. The particular means of coupling a recovery tag to an oligonucleotide primer depends upon the class of compound to which the recoverable tag belongs. When the recovery tag is a polynucleotide, the recovery tag is preferably coupled by polynucleotide linkage, e.g., a phosphate linkage. When the recovery tag is a protein, the recovery tag is preferably coupled by a bifunctional crosslinking agent such as DSS (disuccinimidyl suberate), SPDP (N-succinimidyl 3-(2 pyridyldithio propionate)), SATA (N-succinimidyl S-acetylthioacetate), and the like. Detailed protocols for methods of attaching labels to polynucleotides can be found in, among other places, G. T. Hermanson, *Bioconjugate Techniques*, Academic Press, San Diego (1996).

When the recovery tag on a recoverable primer is a polynucleotide, the recovery tag may comprise all, part, or none of the template-annealing sequence of the recoverable primer. In some embodiments of the invention, the recovery tag may consist of some or all of the sequence of the recoverable primer. In other embodiments of the invention, the recovery tag does not comprise any portion of the template-annealing sequence of the recoverable primer. In still other embodiments of the invention, the recovery tag comprises a balancing polynucleotide. The entire recovery tag may be a balancing polynucleotide. Alternatively, the recovery tag may consist of a balancing polynucleotide and a portion of the template-annealing sequence adjacent to the balancing polynucleotide.

Recoverable primers are capable of specifically hybridizing to target polynucleotide sequences under a given set of hybridization conditions. Criteria for designing sequence specific primers are well known to persons of ordinary skill in the art. Detailed descriptions of primer design criteria that provide for site-specific annealing can be found, among other places, in Dieffenbach and Dveksler, *PCR Primer, A Laboratory Manual, Cold Spring Harbor*, Cold Spring Harbor Press (1995), and Kwok et al, *Nuc. Ac. Res.* 18:999-1005 (1990). The template-annealing sequence portions of the primers are of sufficient length to permit site-specific annealing to template sites of interest. Primers for sequencing are designed to uniquely hybridize to a single template site. The template-annealing sequence of the recoverable primers may be either completely complementary or partially complementary to the bases of the target sequence, i.e., the annealing site. Preferably, the template-annealing sequence of a recoverable primer is completely complementary to the bases of the corresponding target sequence.

"Sequencing ladder" as used herein refers to a set of polynucleotides that is produced from a sequencing reaction, either a chain termination sequencing reaction, e.g., dideoxy sequencing, or from chemical cleavage sequencing, e.g., Maxam and Gilbert sequencing. The process of producing a sequencing ladder is referred to herein as "sequencing ladder generation" or "generating a sequence ladder." Methods for generating polynucleotide sequencing ladders are well known to persons of ordinary skill in the art. Examples of methods of generating a sequencing ladder can be found, among other places, in Sambrook et al, *Molecular Cloning Methods: A Laboratory Manual* Coldspring Harbor, Coldspring Harbor Press (1989). The different polynucleotides, i.e., members, of a specific sequencing ladder, differ in length from one another, but all members of the same ladder comprise the same oligonucleotide primer from which that sequencing ladder is derived. Thus, generating sequencing ladders from a first recoverable primer and a second recoverable primer that anneal to the same template priming site, but differ with respect to the identity of the recovery tags, are said to result in the synthesis of two different sequencing ladders. In addition to being derived from the same primer, the members of a given polynucleotide sequencing ladder are also derived from the same sequencing template. In labeled primer sequencing, four different sequencing ladders, each using a different dideoxy terminating base are generated separately (and may subsequently be combined prior to analysis), even though only a single completed sequence is obtained from combining the information in the four constituent sequencing ladders. When the same recoverable sequencing primer and template are used to generate sequencing ladders in separate reaction vessels, the sequencing ladders produced are said to be different sequencing ladders.

A sequencing ladder generated from a recoverable primer may be referred to as a "recoverable sequencing ladder." "Recoverable sequencing ladder" also includes sequencing ladders that comprise the functional equivalent of recovery tags, such as sequencing ladders produced during non-recovery tag multiplex methods.

A polynucleotide amplification product generated from a recoverable primer may be referred to as a "recoverable amplification product." "Recoverable amplification product" includes amplification products that comprise the functional equivalent of recovery tags, such as sequencing ladders produced during non-recovery tag multiplex methods.

"Specific binding pair" refers to a pair of molecules that specifically bind to one another. Binding between members of a specific binding pair is usually non-covalent. Examples of specific binding pairs include, but are not limited to antibody-antigen (or hapten) pairs, ligand-receptor pairs, biotin-avidin pairs, polynucleotides with complementary base pairs, and the like. Each specific binding pair comprises two members, however, it may be possible to find additional compounds that may specifically bind to either member of a given specific binding pair.

"Polynucleotide amplification reaction" as used herein refers to a broad range of techniques for the amplification of specific polynucleotide sequences. Examples of such amplification techniques include the polymerase chain reaction (PCR), ligase chain reaction (e.g., EP 336731 (Wallace), EP 320308 (Backman), and EP 439182 (Backman)), 3SR (Guatelli et al, *Proc. Natl. Aca. Sci. USA* 87:1874-1878 (1990), and nucleic acid sequence-based amplification (NASB) (van Gemen et al., *J. Virol. Methods* 45:177-188 (1993), for example.

"In separated form" refers to polynucleotides that are eluted from a particular support without significant contamination by polynucleotides that were captured on other supports in the flow path.

"Target polynucleotide" means a polynucleotide that is to be specifically bound to a complementary entity, such as a recovery tag binding compound.

"Polynucleotide population" reference to a collection of polynucleotides that are the same as or different from each other, but which contain a common polynucleotide sequence or a recovery tag. Different polynucleotide populations differ because each different population has a different, distinct common sequence or common recovery tag.

"Sequence-specific capture agent" has substantially the same meaning as "recovery tag binding compound".

II. Apparatus

According to one aspect, the invention provides apparatus which are useful for separating and isolating different-sequence polynucleotides from each other, in separated form.

Figure 2:
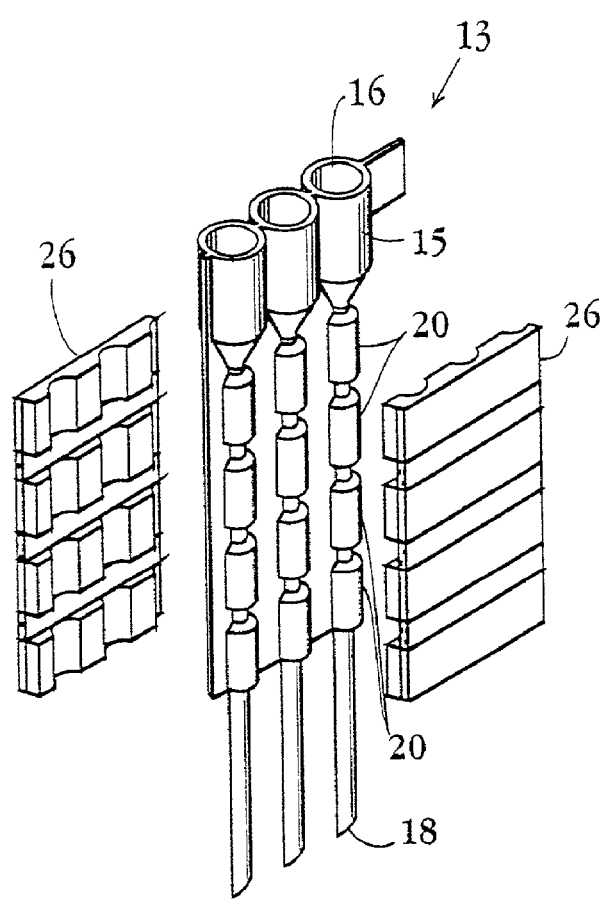
FIG. 2 illustrates a perspective view of a plurality of flow paths in accordance with the invention.

A first exemplary apparatus 12 is shown in FIGS. 1 and 2. Apparatus 12 comprises a column 13 which defines a common flow path 14 extending therethrough. Column 13 includes an increased diameter portion 15 which forms an inlet port 16 into which a polynucleotide mixture can be introduced. In the embodiment shown, inlet port 16 includes a funnel-shaped bottom that is integrally formed with a main body 17 of the column. The main body terminates with an outlet port 18 from which different polynucleotides or different polynucleotides populations can be eluted. A plurality of chambers 20, each of which contains a solid support 22, are provided in series along flow path 14. Although four chambers and corresponding supports are shown in FIGS. 1 and 2, it will be appreciated that fewer or more chambers and supports can be employed, depending on the number of different polynucleotides or populations to be separated. Optionally, the chambers are separated from each other by intervening segments 24 to help hold the supports in place, and also to provide insulation regions between the chambers to improve the specificity of control over the physical properties of the different changes.

For example, main body 17 can be formed from an initially cylindrical tube using a heat-shrinkable plastic. An end of the tube is heated to form outlet region 18 having an inner diameter that is smaller than the initial inner diameter of the tube.

Region 18 thus includes a lower, outlet end for fluid egress, and an upper, inner end which defines a lower end of a first chamber 20. A first support 22 is then placed adjacent to the inner end of region 18, followed by heating and/or mechanical pinching of the tube region immediately above the support to form a completed chamber 20 which encloses first support 22. By repeating the steps of adding a support and then heating or pinching the tube region immediately above the added support to complete additional chambers, a flow path passing through a plurality of supports in series can be formed. A region defining inlet 15 can be added by joining a second tube segment to the top of the first tube and forming a liquid-tight connection by sonic welding, melting, etc. Alternatively, the entire column can be formed from a single tube and, if the inlet region is designed to have a greater outer diameter than the main body, the outer diameter of the main body can be made to be smaller than that of the inlet region by heat-shrinking the chamber walls around the solid supports during formation of the chambers of the column.

With continued reference to FIG. 1, apparatus 12 further includes a multi-piece jacket 26 that is adapted to fit around the exteriors of the chambers. In the embodiment shown, the jacket is formed by joining together two opposing halves which individually surround the different chambers. In more particular embodiments, the jacket may include individual heating coils or electric field generating devices, as described below.

With reference to FIG. 2, a plurality of columns 13 may be formed within a single unit. Similarly, jackets for the parallel columns may be provided in integral halves 26.

Figure 3:
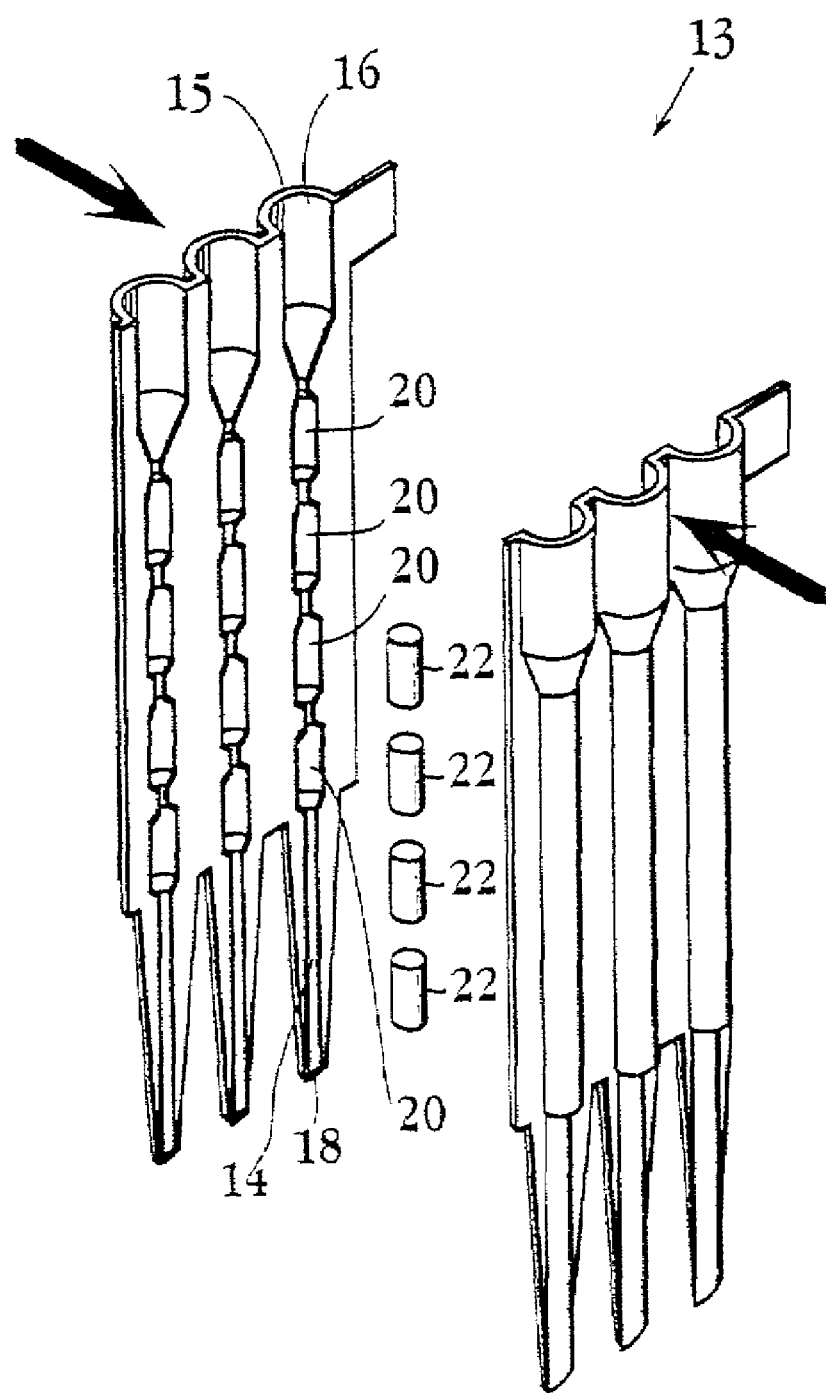
FIG. 3 illustrates an exploded view of another embodiment of the invention comprising a plurality of flow paths that can be formed by combination of two opposing pieces.

FIG. 3 shows another embodiment in accordance with the present invention, wherein the support chambers are formed by matching halves that define a plurality of columns. Each half defines a plurality of serial chambers which are separated by intervening segments which help seat the plurality of chambers. Conveniently, the matching halves may be formed by injection molding to produce monolithic pieces that can be joined together as shown in the Figure.

Figure 4:
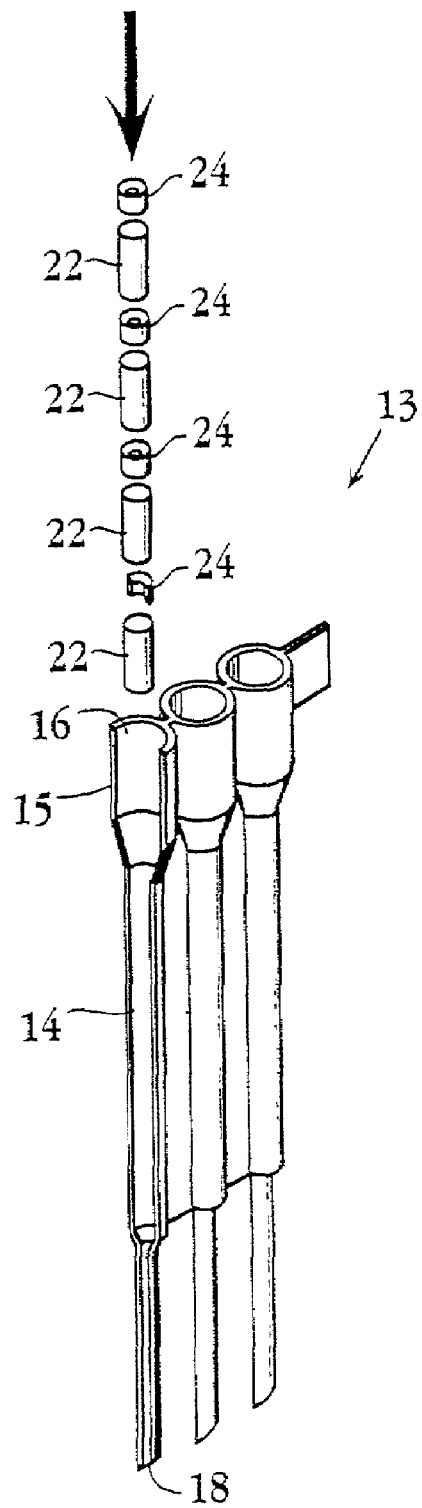
FIG. 4 illustrates another embodiment of a column, showing a perspective view of a plurality of columns formed together, with portions of one column broken away, showing an exploded view of a support/insulator assembly.

FIG. 4 illustrates another column construction wherein the flow path is defined by a cylindrical region 14. In this embodiment, solid supports 22 are separated from each other by separators 24. Thus, the chambers that surround the individual supports are defined by the wall regions of region 14 that immediately surround each support, and which are separated from each other by separators 22. Such an arrangement can be made by inserting alternating supports and insulators into inlet port 15.

Figure 5:
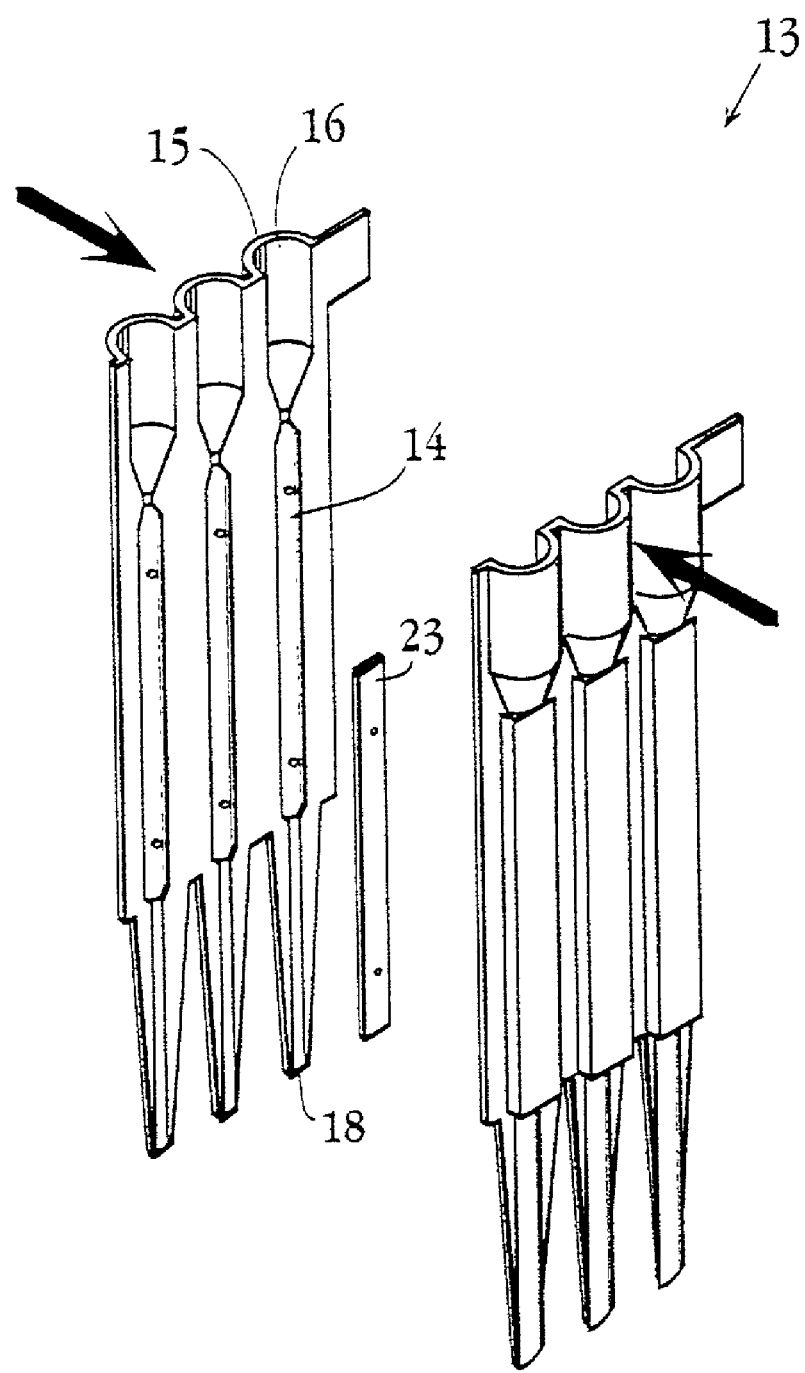
FIG. 5 illustrates yet another embodiment of a column, showing a perspective/exploded view of a plurality of columns.

FIG. 5 illustrates still another construction which employs a monolithic support 23 which is adapted to fit into the column body as shown in the figure, and which comprises a plurality of solid supports having different capture reagents located in series along support 23.

The solid supports used in the present invention can be made of any material that is suitable for the purposes of the invention. In particular, the material must be capable of forming stable covalent or non-covalent bonds with sequence-specific capture agents so that the agents are capable of capturing complementary target sequences from the sample mixture. In addition, the material should have low affinity for polynucleotides other than the target polynucleotides which are to be bound by the capture agent. In one embodiment, the solid supports comprise high density polystyrene, preferably in the form of a cylindrically shaped frit. The solid support preferably occupies a small volume and has high binding capacity. For purposes of illustration only, supports can comprise high density polystyrene with the following properties: pore size: 25-30 µm; length: 0.365"; diameter: 0.128"; void volume: >50%; surface area: 0.26 m$^2$/g. In another embodiment, the supports may comprise controlled pore glass (CPG). In yet further embodiments, the solid support is provided in the form of beads, powder clusters, membranes, or the like, which may be held in place by porous frits or membranes.

The column that contains the supports can be made of any appropriate material that is compatible with the purposes of the invention. The column material should be chemically inert towards, and have low binding affinity for, the polynucleotides that are to be separated. Thus, columns can be made of plastics such as polyethylene, polypropylene, polystyrene, polyacrylamide, polycarbonate, or the like; metals or metal alloys such as aluminum or stainless steel; silicates or coated silicates (glass); polysaccharides; etc. For example, materials used in standard electrophoresis or chromatographic DNA separation methods can be used. Columns formed from multiple materials or components are also contemplated.

As discussed further herein, the device of the invention is used to bind target polynucleotides to different, sequence specific capture agents which are located on different solid supports (or different solid support regions). As a result, a polynucleotide mixture can be "deconvoluted" into separate components or separate polynucleotide populations. These separated polynucleotides can then be released specifically from individual supports and eluted in separate form, substantially free from contamination by other polynucleotides in the mixture which are still bound to other supports in the flow path. Although polynucleotide release from selected supports can be accomplished manually, automation of this process is preferable. Accordingly, operation of the invention is described below with respect to configurations that allow computer controlled automation of various steps.

For example, a control mechanism in communication with the supports can be used to selectively alter a physical property of a particular support, in order to denature and thereby release captured polynucleotides from that support, so that the released polynucleotides can be eluted separately from polynucleotides captured on other supports. In one embodiment, during alteration of the physical property of the particular support, the other supports remain unchanged.

Figure 6:
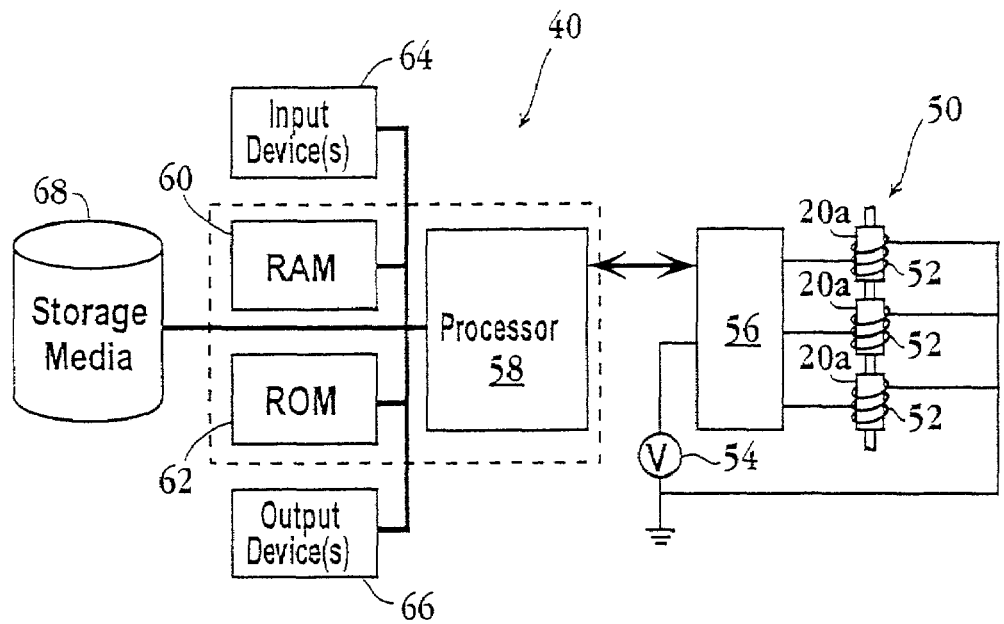
FIGS. 6 and 7 show functional block diagrams of different control mechanism in accordance with the invention.

FIG. 6 illustrates an embodiment wherein the control mechanism comprises a temperature control unit 50 which includes an individually controllable heating/cooling element 52. Although element 52 is shown as a heating coil in the Figure, equivalents thereof can also be used, such as a peltier device. An element 52 is positioned adjacent to or around the outer wall 20a of each chamber, and can be embedded within a jacket 26 such as described above.

In this embodiment, each column is made so that the chamber walls surrounding the solid supports have high thermal conductivity to readily transfer heat to and from the solid supports. However, in arrangements where the supports are selectively heated, heat transfer between different chambers, i.e., along the length of the column, should be low enough to avoid release of polynucleotides from non-selected supports. For this purpose, exterior wall regions located between serial chambers can be formed from materials having low thermal conductivity, or may be surrounded by external insulation layers that help maintain temperature stability in those regions. Alternatively, or in addition, adjacent solid supports can be separated by insulation materials that occupy a portion of the flow path between the supports but which allow adequate fluid flow for elution.

In FIG. 5, heating/cooling elements 52 are incorporated into a circuit which also includes a voltage source 54 and a switch 56 for selecting which element 52 is to be adjusted at a particular time. In the illustrated configuration, one terminal for each element 52 is connected to a first terminal of the voltage source, while a second terminal for each element 52 is connected is to the output terminal of switch 56. The input terminal of switch 56 is connected to the other terminal of voltage source 54. The switch may be manually operated or may be programmed to control the activation and timing of activation or adjustment of each heating/cooling element. Appropriate circuitry may also be included in the switch to control the amount of heat generated by the coil(s).

In one embodiment, the switch is processor-controlled. Processor 58 may be a microprocessor which is embedded in the switch itself or may be part of a computer system 40 which includes other computer components such as random-access memory (RAM) 60, read-only memory (ROM) 62, input devices 64, such as a keyboard and mouse, output devices 66, such as a monitor and printer, and a storage media 68 such as an internal or external hard disk.

The programming of the switch may be implemented with software which may be fetched from RAM and executed by the processor. The software may be stored in storage medium 68 which may be any suitable medium, including various magnetic media such as disks or tapes, and various optical media such as compact disks. The software may also be conveyed to computer 40 over communication paths throughout the electromagnetic spectrum including signals transmitted over a network or the internet and carrier waves encoded to transmit the software. Alternatively, the programming of the switch may be implemented with functionally equivalent hardware using discrete components, one or more application specific integrated circuits (ASICs), digital signal processing circuits, or the like. Such programmed hardware may be physically integrated with the processor or may be a separate component which may be embodied on a computer card that can be inserted into an available slot in the computer. Thus, the programming of the switch may be implemented using software, hardware, or combination thereof. It will be apparent to one skilled in the art of programming to implement a system to perform necessary control processes.

Figure 7:
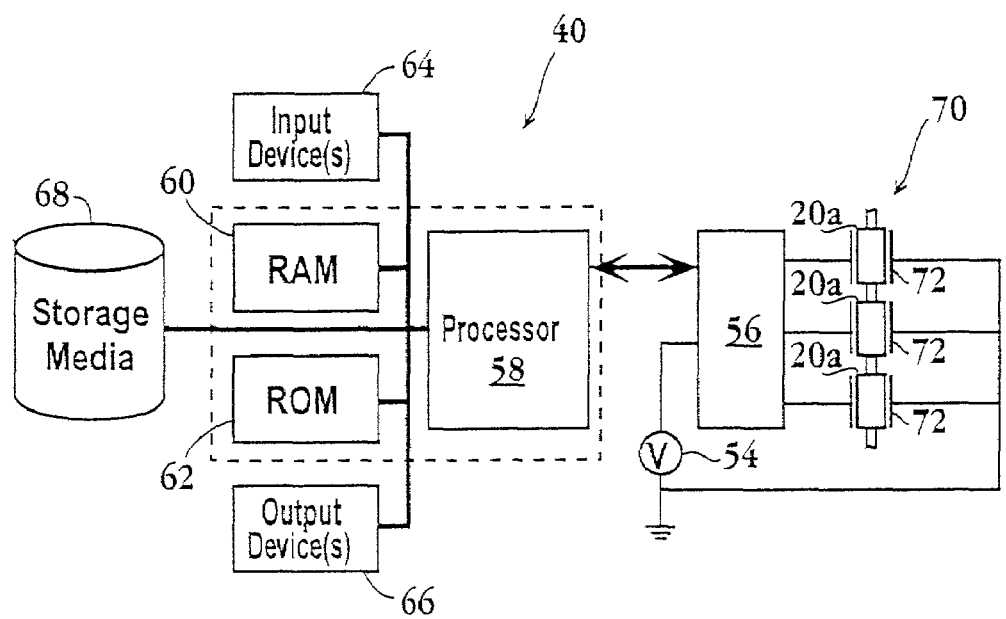

In another embodiment, illustrated in FIG. 7, the control mechanism comprises a circuit including a device 70 for selectively applying an electric field (or voltage potential) to the different supports. Such a circuit is generally similar to the circuit shown in FIG. 6, and like components are identified with like reference numerals. However, as shown schematically in FIG. 7, the electric field (or voltage potential) applying circuit includes a pair of capacitor plates 72, or equivalents thereof, for each support, instead of heating/cooling elements. In this embodiment, switch 56 is configured to selectively apply an electric field to a selected one or more of the supports. Each pair of capacitor plates is symmetrically positioned about a respective one of the support chambers. The plates are preferably shaped to follow the contour of the chambers.

In this embodiment, each column is constructed to have high electrical conductivity across the chamber walls. Preferably, the electrical conductivity in wall regions between the chambers, i.e., along the length of the column, should be low enough to avoid releasing polynucleotides from non-selected supports. Thus, the chamber walls between consecutive chambers may be impregnated with an electrically insulating material.

In the illustrated arrangement, a plate in each capacitor plate pair is connected to one of the terminals of the voltage source, while the other plate is connected to the output terminal of the switch. The input terminal of the switch is connected to the other terminal of the voltage source.

The switch may be manually operated or may be programmed to control the capacitor plate pair(s) to which a voltage is applied, the magnitude of voltage applied, and the time during which a given voltage is applied to a given capacitor plate pair. Appropriate circuitry may also be included to apply different voltages to different capacitor plate pairs at the same time. Such variables may be adjusted to accommodate different electrical binding affinities in the different groups of sequence-specific capture agents. As described for the previous embodiment, programming of the switch may be implemented using software, hardware, or a combination thereof.

Processes in accordance with the invention can be automated using apparatus as described above, to control sample loading, content and flow rate of solvent, selective polynucleotide release, and polynucleotide collection. A typical process begins with introduction of the sample into the flow path through an input port as discussed above. The physical properties (physical conditions) of the supports are set to be in a target-binding state so that each support is able to specifically capture polynucleotides that contain sequences or recovery tags that are complementary to the support-bound tag binding compounds. For supports whose binding properties are controlled by temperature, the supports can be set to room temperature or a somewhat higher temperature, such as 30° C., 35° C., or 40° C., so that non-target polynucleotides pass through the supports without binding to them, and only target polynucleotides are bound to the appropriate supports. The flow rate of sample through the flow path is chosen to allow sufficient time for target polynucleotides to bind to the binding compounds on the supports, according to known hybridization principles and using empirical optimization if necessary.

In one embodiment, sample flow is performed continuously during the loading step, at a continuously positive flow rate. In a second embodiment, solvent flow is alternated between a positive flow rate and stopped flow, so that when flow is stopped, the polynucleotides in the sample have additional time to bind to complementary binding compounds on the supports. In a third embodiment, the direction of flow is reversed at least once per support so that the sample can be passed back through each supports to increase capture of target polynucleotides. Solvent flow may be continued until most or all of the non-target polynucleotides have been washed from the supports.

After binding (hybridization) is complete, bound polynucleotides are released from selected supports into the flow path by altering a physical property of the corresponding support. For example, this may be performed by selectively heating the supports. That is, the heating element associated with a support on which a specific polynucleotide population (i.e., the $i^{th}$ population) resides, is activated to denature the polynucleotides in that population. Concurrently with, or after, the denaturing, a suitable elution solvent is introduced into the flow path to elute the released $i^{th}$ population of polynucleotides through the flow path for separate collection.

If there are other populations of polynucleotides to be eluted, variable i can be increased by 1, and the process returns to the previous step in which another population of polynucleotides is released by activation of the support on which that population resides. The steps of release and elution of specific populations of polynucleotides are repeated until all of the populations have been individually collected.

III. Methods

The present invention is useful for separating and isolating different-sequence polynucleotides. These polynucleotides can be from any source or produced by any appropriate method. Preferably, the polynucleotides contain unique recovery tags that permit localized capture on different, tag-specific binding compounds that are immobilized on a series of solid supports in the flow path.

In one embodiment, the polynucleotides comprise a plurality of sequencing ladders derived from different templates. In another exemplary embodiment, the polynucleotides comprise a plurality of different-sequence PCR products, which may be prepared by methods described in PCT Pub. WO 94/21820 (Wallace), for example. In another embodiment, the polynucleotides are products of template-dependent probe ligation or gap-filling ligation, as described for example in U.S. Pat. No. 4,988,617 (Landegren) and U.S. Pat. No. 5,242,794 (Whiteley), EP 320308 (Backman), EP 439182 (Backman), PCT Pub. WO 90/01069 (Segev), EP 336731 (Wallace), and PCT Pub. WO 97/31256 (Barany). In yet another embodiment, the polynucleotides comprise a plurality of primers extended by a single-base, as described for example WO 93/25563 (Wallace). In other embodiments, the polynucleotide mixture is produced by 3SR (Guatelli et al, *Proc. Natl. Aca. Sci. USA* 87:1874-1878 (1990), or nucleic acid sequence-based amplification (NASB) (van Gemen et al., *J. Virol. Methods* 45:177-188 (1993). Polynucleotide mixtures produced by any other methods are also contemplated.

For convenience, operation of the invention is discussed below mainly with reference to separation and isolation of sequencing ladders and PCR products. However, it will be apparent to one of skill in the art how the invention can be used with other polynucleotide mixtures.

Thus, one embodiment relates to methods for simultaneously generating a plurality of polynucleotide sequencing ladders, typically in a single reaction vessel (or in a plurality of vessels whose products are combined after amplification), and analyzing the sequence information derived from the simultaneously generated sequencing ladders. Each sequencing ladder is formed from a recoverable primer having a unique recovery tag. Each polynucleotide member of a polynucleotide set that constitutes a sequencing ladder is labeled with essentially the same recovery tag (or a functional equivalent of a recovery tag). After the simultaneous generation of multiple sequencing ladders, the different polynucleotide sequencing ladders are separated from one another by binding of the recovery tags (or functional equivalents of recovery tags) to recovery tag binding compounds that are immobilized on the solid supports in the apparatus discussed above. Protocols for forming sequencing ladders are well known to persons of ordinary skill in the art. Chain termination sequencing is a preferred method of sequencing ladder generation.

Numerous protocols for chain termination sequencing of polynucleotides have been published. Such protocols may be used for simultaneously generating a plurality of polynucleotide sequencing ladders (and separating the ladders generated) so as to realize significant savings with respect to costly reagents such as thermostable enzymes, fluorescently labeled primers, and fluorescently labeled terminators. Conventional polynucleotide sequencing techniques usually employ at least 8 to 12 units of Taq DNA polymerase for each sequence ladder generated. The term "unit" as used herein with respect to the thermostable polymerase sold under the name Ampli-Taq DNA polymerase (Perkin Elmer, Applied Biosystems Division, Foster City, Calif.) is defined as the amount of enzyme that will incorporate 10 nmol dNTP's into acid insoluble polynucleotide material in 30 minutes at 74° C.; this definition may be used to determine corresponding amounts of other thermostable DNA polymerases. It will be appreciated by those skilled in the art that the foregoing definition of "unit" may be applied to many DNA polymerases and is not limited to AmpliTaq DNA polymerase. Thus, by employing the methods of the invention, sequencing ladders may be produced by using approximately 4 to 6 units (for two-fold multiplexing), or less, of DNA polymerase for each sequencing ladder generated. It will also be appreciated by those skilled in the art that a variety of different DNA polymerases, both thermostable and heat-labile, may be used for sequence ladder generation and that similar degrees of reductions in reagent usage can be achieved with different DNA polymerases. Numerous different DNA polymerases or mixtures of DNA polymerases may be used for sequence ladder generation. When the sequence ladders are generated through cycle sequencing, the DNA polymerase used is preferably a thermostable DNA polymerase. Examples of suitable thermostable DNA polymerases include Taq™ (Perkin-Elmer, Norwalk Conn.), Vent™ (New England Biolabs, Beverly Mass.), Deep Vent™ (New England Biolabs, Beverly Mass.), Pyrococcus furiosus DNA polymerase (Stratagene, La Jolla Calif.), Thermotoga maritima DNA polymerase, and Ampli-Taq DNA polymerase, FS™ polymerase, and Ampli DNA polymerase, Taq FS DNA polymerase. Taq™ FS DNA polymerase (Perkin-Elmer, Norwalk Conn.) is particularly preferred for use in cycle sequencing.

Multiplex sequencing involves the simultaneous generation of a plurality of polynucleotide sequencing ladders in the same solution. The method comprises the step of mixing a plurality of recoverable sequencing primers with one or more sequencing templates. The mixing may take place in a single reaction vessel. The act of mixing comprises placing the recoverable primers and the templates into the same solution, thereby permitting the primers to anneal at specific sites on the template (or templates) so that the primers may be extended. Optionally, the reaction vessels may be agitated to improve mixing of the solution components. The reaction vessel serves as a container for the primers, templates, enzymes, dNTPs, chain terminators, and other reagents required for sequence ladder generation. The reaction vessel may take on any of a variety of shapes and sizes that would be known to a person of ordinary skill in the art, such forms include, but are not limited to, Eppendorf tubes, sealed capillary tubes, covered multi-well plates, and the like. After or concurrently with the mixing step, the recoverable sequencing primers are subjected to conditions that permit the recoverable primers to hybridize (anneal) to their respective templates. The plurality of templates used in the subject methods may be present on the same or different polynucleotide molecules. For example, a single chromosome or plasmid may comprise a plurality of sequencing templates if the recoverable primers are selected so as to anneal to multiple regions of the same DNA molecule. Alternatively, individual recoverable primers may be designed to hybridize to a plurality of templates that are present as separate DNA molecules. Recoverable primers designed for sequencing may be used to prime both strands of the same polynucleotide sequence during the same sequence generating reaction. Examples of sequencing templates include chromosomal DNA, cDNA, RNA, or DNA inserted into cloning vectors, and the like. Optionally, the templates for sequencing may be polynucleotides generated by nucleotide amplification reactions such as PCR (polymerase chain reaction).

Preferably, sequencing ladders are formed by cycle-sequencing. A description of cycle sequencing can be found, among other places, in Murray V., *Nucl. Acid. Res.*, 17:8889 (1989). Typically, cycle-sequencing is a sequencing ladder generating technique comprising the following steps: (a) hybridization of an oligonucleotide primer to a template for sequencing so as to form a primed template, (b) extending the primer with a DNA polymerase, (c) ending the extension reaction with a chain terminator (e.g., a dideoxynucleotide terminator), (d) denaturing the primed template, (e) repeating steps (a) to (d) for multiple cycles. Increasing the number of cycles may be used to increase the amount of labeled polynucleotide produced, thereby compensating for relatively small amounts of starting material.

In embodiments of the invention in which the recoverable primers anneal to the same strand of the same template, the annealing sites on the templates may be sufficiently close to one another so that interactions between the two sites during sequencing ladder generation may be detected. For example, a first sequencing primer and second sequencing primer may be selected to anneal to the same chromosome such that the first primer anneals about 400 bases 5' with respect to the annealing site of the second primer. The intensity of the sequence ladder signal, i.e., the quantity of polynucleotide constituents of the sequencing ladder, produced from the first primer falls off abruptly (though not to undetectable levels) when the sequence ladders extends through the annealing site of the second primer. This decrease in intensity may be used to determine when the sequence information obtained from two primers is contiguous.

Any of a variety of chain terminator sequencing may be used to obtain sequence information from a given template. The different methods may involve variations in parameters such as the site of labeling (on the primer or on the chain terminator); the identity of the labels employed, the number of different labels employed, and the like.

For labeled terminator sequencing, sequence information may be obtained from a given template and a single recoverable primer by using four chain terminators, each chain terminator corresponding to a different nucleotide base and labeled with a distinctive fluorescent label.

For labeled primer sequencing, the recoverable primers are labeled and four distinct recoverable primers, each annealing to the same template site, but having a distinctive fluorescent label, are used in four separate reaction vessels to obtain the sequence of each template in the multiplexed sequencing reaction. For example, a first set of four labelled recoverable primers are prepared to prime at the same location on a given template. Each of these primers in the set is labeled with a different detectable label (four spectrally distinct labels are used). The recovery tag on each of the primers in a set is labeled with the same or different recovery tags (preferably the same recovery tag is used for each member of the set). Additional four primer sets are prepared for each template to be sequenced. The different members of each set of primers are then distributed between four reaction vessels, such that each vessel contains multiple primers (and templates) but only one primer from each primer set. A sequencing reaction is then prepared in each vessel, using a single type of chain terminating dideoxynucleotide in each vessel (A, G, C, or T). Each primer can be labeled with the same label or with or different labels. Alternatively, labels can be introduced to sequencing products using labeled terminators, for example.

Suitable fluorescent labels which may be used in practicing the invention include, but are not limited to, 6-carboxyfluorescein (6-FAM), 5-carboxyfluorescein (5-FAM), 6-carboxy-4,7,2',7'-tetrachlorofluorescein (TET), 6-carboxy-4,7,2',4',5',7'-hexachlorofluorescein (HEX), 5-(and 6)carboxy-4',5'-dichloro-2'7'-dimethoxyfluorescein (JOE), and 5-carboxy-2', 4',5',7'-tetrachlorofluorescein (ZOE), tetramethylrhodamine (TAMRA), 4,7-diclorotetramethyl rhodamine (DTAMRA), rhodamine X (ROX), rhodamine 6G (R6G), rhodamine 110 (R110), and the like. Descriptions of suitable fluorescent labels can be found, for example, in U.S. Pat. No. 5,366,860 (Bergot), U.S. Pat. No. 5,188,934 (Menchen), U.S. Pat. No. 5,654,442 (Menchen), U.S. Pat. No. 6,020,481 (Benson), U.S. Pat. No. 5,863,727 (Lee), U.S. Pat. No. 5,847,162 (Lee), U.S. Pat. No. 6,008,379 (Benson), and U.S. Pat. No. 5,936,087 (Benson), for example.

Non-fluorescent labels may also be used, such as enzymatic labels, radioactive labels, chemiluminescent labels, etc.

As discussed above, the recovery tag binding compounds are located on distinct solid supports (or distinct regions of a monolithic support) which are located in series in a flow path. The recovery tag binding compounds are attached to the solid support in a manner so as to permit the recovery tag binding compounds to interact with their respective recovery binding tags. The recovery tag binding compounds may be attached to the support through either direct or indirect linkages. The term "direct linkage" refers to the covalent binding of the recovery tag binding compound to the solid support, including covalent bonding through a linker (and optionally a spacer arm). The term "indirect linkage" refers the binding of the of the recovery tag binding compound to the solid support through a specific binding pair, e.g., biotin-avidin (or streptavidin) pairs or antigen-hapten, wherein one member of the pair is joined to the recovery tag binding compound and the other member of the pair is joined to the solid support.

A variety of techniques may be used to immobilize the recovery tag binding compounds on the solid supports. The specific techniques selected will depend upon the choice of recovery tag binding compounds and solid support materials. Techniques for immobilizing proteins and polynucleotides are well known to persons of ordinary skill in the art of molecular biology. For example, proteins may be conjugated to solid supports through formaldehyde, DMS (dimethyl suberimidate), and reductive amination. Polynucleotides may be conjugated to solid supports through agents such as 1,3-diaminopropane, 3,3'-iminobisproplyamine, EDC (1-ethyl-3-(3-dimethylaminopropyl)carbodiimide hydrochloride), SPDP (N-succinimidyl 3-(2pyridyldithio propionate)), and SATA (N-succinimidyl S-acetylthioacetate). Examples of moieties for linking oligonucleotides to solid supports can be found in Pon et al, *Biotechniques*, 6:768-775 (1988); U.S. Pat. No. 4,659,774 (Webb); WO 92/04384 (Barany et al.); Brown et al, *J. Chem. Soc. Commun.*, 1989:891-893; Dahma et al, *Nucleic Acids Res.* 18:3813-3821 (1990); Beattie et al, *Clinical Chemistry*, 39:719-722 (1993); and Maskos and Southern, *Nucleic Acids Res.* 20:1679-1684 (1992).

The strength of binding between a binding compound and its complementary recovery tag can be characterized by a melting temperature, Tm, which defines a temperature at which 50% of either the tag or the binding compound is bound to the other. In a preferred embodiment, the recovery tags and recovery tag binding compounds are polynucleotides. For polynucleotides, melting temperatures are a function of several factors, such as sequence composition, length of complementary regions, salt concentration, pH, solvent composition (aqueous vs organic), and concentration of binding partners (tag and complementary binding compound) and can be calculated using any of a variety of predictive methods. Exemplary methods can be found in Breslauer et al., *Proc. Natl. Acad. Sci.* 83:3746-3750 (1986); Rychlik et al., *Nucleic Acids Res.* 17:8543-8551 (1989) and 18:6409-6412 (1990); Wetmur, *Crit. Rev. Biochem. Mol. Biol.* 26:227-259 (1991); Osborne, *CABIOS* 8:83 (1991); and Montpetit et al., *J. Virol.*

*Methods* 36:119-128 (1992)). Typically, complementary polynucleotide sequences are between 15 and 36 nucleotides in length. Complementary sequence lengths of 18 to 24 nucleotides are preferred because such polynucleotides tend to be very sequence-specific when the annealing temperature is set within a few degrees of an oligonucleotide melting temperature (Dieffenbach, supra). Binding interactions can be further optimized by empirical methods, if desired.

After a polynucleotide mixture has been prepared (e.g., a sequencing ladder), the polynucleotide mixture is introduced into the inlet of the flow path of the apparatus in any appropriate way, such as by pumping, gravity flow, or vacuum loading. As the sample mixture passes through the series of supports, polynucleotides that are complementary to the binding compounds on the first support are captured thereon by specific binding interactions, while the other polynucleotides in the mixture continue moving to the next support, until the mixture has passed through all of the supports. Sample loading is preferably performed under conditions such that binding of non-target polynucleotides to the capture compounds is minimal. Thus, loading should be performed at a temperature that is (1) well below (e.g., at least 10° C. below) the lowest Tm of the capture compounds for binding to their complementary tag sequences, and (2) well above (e.g., at least 10° C. above) the highest Tm value of the capture compounds for binding non-complementary sequences that may be present in the sample. By binding the recovery tags to their cognate recovery tag binding compounds, the sequencing ladders (or any other fragments that are to be captured) are separated from one another and purified.

Prior to passage through the supports, the polynucleotide mixture may be modified by adding reagents that enhance binding between the recovery tags and the recovery tag binding compounds (e.g., to alter pH, ionic strength, or salt concentration of the mixture). Binding between the recovery tags and the recovery tag binding compounds may also be modified by the addition of DNA binding proteins or other DNA binding compounds. Contact between the immobilized recovery tag binding compounds and the recovery tags should be for a period of time sufficient to permit the binding of a detectable amount of polynucleotide to the immobilized recovery tag binding compounds. The amount of time (or flow rate) that permits sufficient binding of the recovery tags may vary, depending on the specific recovery tag and recovery tag binding compounds that are used, concentration, etc. The kinetics of nucleic acid hybridization and denaturation are well understood and may be used to calculate the time and conditions required for binding and release. Information on hybridization kinetics can be found in U.S. Pat. No. 5,935,793 (Wong) and references cited therein, Berger and Kimmel, *Guide to Molecular Cloning Techniques*, Academic Press, San Diego (1987), Cantor and Schimmel, *Biophysical Chemistry Part III: The Behavior of Biological Macromolecules*, W. H. Freeman, NY (1980), and Saenger, *Principles of Nucleic Acid Structure*, Springer-Verlag, New York (1989), for example. See also WO 98/14610 and counterpart U.S. Pat. No. 6,124,092, both incorporated herein by reference, which, among other things, contain examples of experimental conditions that can be used in performing parts of the present invention. Successful results can be obtained without binding all (or even a substantial portion) of the polynucleotides. After the sample has passed through the last serial support, the column of supports can be washed with additional solvent or a washing solution to remove non-specifically bound materials, if necessary.

After loading has been completed, selected polynucleotides or polynucleotide populations can be released from selected, individual supports and eluted from the column for collection. As discussed above, release of bound polynucleotides can be accomplished by altering a physical property of the support, such as temperature or electrical potential, such that the support is changed from a tag-binding state to a target-non-binding state. The released polynucleotides can then be eluted from the column by solvent flow, until the released polynucleotides have passed, in separated form, through the column outlet for collection.

The bound polynucleotides can be released from the different supports in any order. For example, for a pumping arrangement that pumps solvent unidirectionally through the column, the supports can be activated for polynucleotide release starting with the support farthest from the column outlet, followed sequentially by the adjacent support closer to the outlet, and so on, until all supports have been cleared of their bound polynucleotide. In an alternative approach, the supports can be activated starting with the support closest to the column outlet, followed sequentially by the adjacent support which is farther from the outlet, until all supports have been cleared. This latter approach may be preferable to reduce premature elution of polynucleotides from downstream supports that may occur when polynucleotides are released and eluted from an upstream support. Different patterns of support activation can also be used.

Sets of recoverable primers that have recovery tags capable of being released under the same or similar denaturation or releasing conditions are referred to herein as "integrated" sets of recoverable primers. One advantage of using integrated sets of primers is that polynucleotide capture on the different supports can be performed under approximately the same conditions, so that control of the conditions of the support can be simplified. In order to provide an integrated set of primers, the recovery tags on the primers are selected so as to have Tm's that are within 15° C. of each other, preferably, within 10° C., and more preferably within 5° C. of each other. The Tm is the denaturation temperature as measured between the immobilized recovery tag binding compound and the recovery tag. The Tm may be determined either empirically or by reference to empirically determined formulae for Tm calculation. Examples of such formulae can be found among other places in Berger and Kimmel, *Guide to Molecular Cloning Techniques*, Academic Press, San Diego, (1987), Cantor and Schimmel, *Biophysical Chemistry Part III: The Behavior of Biological Macromolecules*, W. H. Freeman, NY, (1980), Saenger, *Principles of Nucleic Acid Structure*, Springer-Verlag, New York (1989), and the like.

A releasing step is performed to provide for the analysis of the released polynucleotides. The releasing step should be performed in such a manner so as to maintain the separation of the different sequencing ladders that was introduced during the binding of the recovery tags to the immobilized recovery tag binding compounds.

When the recovery tags and recovery tag binding compounds are both polynucleotides, release is preferably achieved by denaturation of the duplex (or possibly triple helix) formed between the recovery tags and their corresponding recovery tag binding compounds. Factors influencing the denaturation temperature of multi-stranded polynucleotides, e.g., cation concentration, are well known to persons of ordinary skill in the art of molecular biology. Accordingly, release of the polynucleotide recovery tags may be achieved by subjecting the bound polynucleotides to elevated temperatures or the addition of denaturing agents such as urea or formamide in appropriate concentrations.

Collection of the released polynucleotide sequencing ladders (or any other class of polynucleotides that is being isolated) may be achieved by numerous different techniques and configurations of devices used to collect the released polynucleotides. For example, the released sequencing ladders can be collected separately in individual collection vessels, such as tubes or microtiter dish wells, and stored for loading onto a polynucleotide separation device. Such devices are commercially available from a variety of sources, such as an ABI 377, ABI 310, 3700, or 3100 instruments available from Applied Biosystems, Foster City, Calif. Descriptions of automated sequencing apparatus can be found, for example, in U.S. Pat. Nos. 4,232,769, 4,603,114, 4,704,256, 4,811,218, 5,277,780, 5,290,419, 5,307,148, 5,366,608, 5,384,024, and 5,543,026.

Preferably, collection of the released polynucleotides, such as sequencing ladders, is integrated directly with a polynucleotide separation device, e.g., a multicapillary electrophoresis device for analysis of the polynucleotides.

The invention permits the multiplexing of sequencing reactions, amplification reactions, other types of primer extension reactions, and other polynucleotide mixtures to varying degrees. The sequencing reactions may be multiplexed by a factor of two or more. Typically, multiplexing will be by a factor of between 2 and 20. For example, in one embodiment, the factor is 5, 10, 15, or 20. In another embodiment, the factor is 5 or less, 10 or less, 15 or less, or 20 or less. However, the invention also includes embodiments in which multiplexing is by a factor greater than twenty.

Although the foregoing discussion has been primarily concerned with multiplex methods of sequencing, it will be readily appreciated by persons skilled in the art that the general principles of the invention can readily be adapted to virtually any molecular biology technique involving probe ligation, probe cleavage, or primer extension. For example, by using a plurality of recoverable primers, each having a unique recovery tag (or functional equivalent thereof), multiple primer extension reactions may be performed simultaneously and the reaction products subsequently separated on the basis of binding to immobilized recovery binding tag compounds. These numerous multiplexed methods of primer extension reactions used are considered to be embodiments of the subject invention. Chain termination sequencing (Sanger method) and PCR are examples of primer extension reactions.

Thus, in another embodiment, the invention also provides methods for separating a plurality of simultaneously generated polynucleotide amplification products. This can be accomplished by modifying the above discussion regarding sequencing ladders so as to generate recoverable polynucleotide amplification products rather than recoverable sequencing ladders. Methods for polynucleotide amplification are well known to persons of ordinary skill in the art. Detailed protocols for polynucleotide amplification can be found in, among other places, Dieffenbach and Dveksler, *PCR Primer, A Laboratory Manual*, Coldspring Harbor Press, Coldspring Harbor, N.Y. (1995), McPherson et. al, *PCR A Practical Approach, Vol* 1, IRL Press Oxford, England (1991), McPherson et. al, *PCR A Practical Approach, Vol* 2, IRL Press Oxford, England (1995), U.S. Pat. Nos. 4,683,202, 4,683,195, and 4,965,188. Furthermore, detailed protocols for multiplex PCR can be found in, among other places, Shuber et al, Genome Research, 5:488-493 (1995), Eggerding, *PCR Methods and Applications*, 4:337-345 (1995), Cuppens et al, *Molecular and Cellular Probes*, 6:33-39 (1992), and U.S. Pat. No. 5,582,489.

The methods of separating a plurality of simultaneously generated polynucleotide amplification products involve performing polynucleotide amplification reactions, wherein at least one member of a pair of amplification primers is a recoverable amplification primer. When both members of a pair of amplification primers are recoverable primers, the amplification products produced will have two recovery tags. When both members of a pair of amplification primers are recoverable primers, the recovery tags may be the same or different from one another. The invention also includes embodiments in which recovery tags and recovery tag binding compounds may be selected so as to provide for the isolation of selected sets of nucleic acid amplification fragments rather than the isolation of individual amplification fragments. Generally, the subject methods of separating a plurality of simultaneously generated polynucleotide amplification products (through multiplex PCR or similar amplification techniques) include the steps of mixing a plurality of recoverable amplification primers having recovery tags with a plurality of amplification templates. After the mixing step, the amplification templates are amplified using at least one recoverable primer so as to form a plurality of amplification products, each product having a recovery tag, wherein the amplification reaction is in a single reaction vessel. Next, the recovery tags, and hence the amplification products, are permitted to bind to recovery tag binding compounds that have been immobilized on a solid support in a spatially addressable manner. Subsequently, the bound amplification products are released from the solid supports and individually collected.

The invention may also utilize recoverable primers having oligonucleotide recovery tags that cannot be replicated during a nucleic acid amplification reaction. Thus, when such primers are employed in polynucleotide amplification reactions, an extension product complementary to the recovery tag is not generated. These recoverable primers are referred to herein as "hinged primers." Hinged primers are particularly useful in multiplex polynucleotide amplifications as described herein because there is no need to denature (or prevent from renaturing) a double-stranded polynucleotide comprising the recovery tag so that the recovery tag may bind to a recovery tag binding compound that is a complementary oligonucleotide. Recoverable primers that comprise a recovery tag that can be replicated during nucleic acid amplification generate a polynucleotide sequence complementary to the recovery tag sequence during the process of polynucleotide amplification. This complementary sequence can significantly compete with the binding of a recovery tag to an immobilized recovery tag binding compound (e.g., an immobilized complementary oligonucleotide). Accordingly, hinged primers may be advantageously employed in many of the methods of the invention where it is desirable to efficiently recover the amplification products.

There are many different oligonucleotides that may be used as recovery tags that cannot be replicated during a nucleic acid amplification reaction. In one embodiment of hinged primers, the recovery tag is an oligonucleotide analog that is not capable of being replicated by the DNA polymerase used in the amplification reaction. Examples of such non-replicable oligonucleotide analogs include, but are not limited to peptide-nucleic acids (PNAs) and the like. PNAs synthesis and structure is described in, among other places, Egholm et al, *J. Am. Chem. Soc.* 114:1895-1897 (1992), Kosynkina et al, *Tet. Lett.* 35:5173-5176, Dueholm et al, *J. Org. Chem.* 59:5767-5773 (1994). In another embodiment of hinged primers, the recovery tag may be an oligonucleotide that could otherwise be replicated by a DNA polymerase, but is blocked by a non-replicable linker joining the recovery tag to template-annealing sequence portion of the recoverable primer. Such non-replicable linker may be oligonucleotide analogs. Alternatively, the non-replicable linkers have little or no structural similarity to naturally occurring polynucleotides. Examples of non-replicable linkers that are oligonucleotide analogs include poly-5' to 3'-deoxyribose (i.e., DNA without nucleoside bases), peptide nucleic acids and the like. Examples of non-replicable linkers that are not oligonucleotide analogs include polyethylene glycol, hydrocarbons, and the like. Methods of conjugating linkers to polynucleotides are well know to those of ordinary skill in the art, examples of such conjugation techniques can be found in Hermanson, *Bioconjugate Techniques*, supra. Typically, the non-replicable linker is located at the 5' end of the template-annealing region of the hinged primer, thereby minimizing interference with the activity of the DNA polymerase catalyzing the extension reaction. Alternatively, the recovery tag of a hinged primer may be rendered non-replicable in an amplification reaction by virtue of the site of attachment (or orientation) of the recovery tag to the primer, e.g., at a position other than the 5' end primer.

Although the foregoing discussion is focused primarily on using recoverable primers for multiplexed sequencing ladders or polynucleotide amplification, it will be appreciated that the methods may be readily adapted for use without recoverable primers. Oligonucleotide primers without recovery tags may be used to generate recoverable sequencing ladders or recoverable polynucleotide amplification products; these methods are referred to as "non-recovery tag multiplex methods." Non-recovery tag multiplex methods employ the functional equivalents of recovery tags. In non-recovery tag based embodiments, primers without recovery tags may be substituted for recoverable primers by using recovery tag binding compounds that are polynucleotides comprising a polynucleotide sequence capable of specifically hybridizing to a polynucleotide sequence that is newly formed during either sequencing ladder generation or the process of polynucleotide generation. These newly generated polynucleotide sequences are the portions of the polynucleotide ladder or amplicon other than the primer sequence. Suitable recovery tag binding compounds for use with such primers may specifically bind to either a newly synthesized polynucleotide region or to a combination of a newly synthesized polynucleotide region and a primer polynucleotide region that is immediately adjacent to the 3' end of the primer.

The recovery tag binding compounds may be designed to bind to newly generated polynucleotide sequences that are on the polynucleotide strand complementary to the polynucleotide strand comprising the primer. For example, a recovery tag binding compound may be a polynucleotide complementary to the polynucleotide sequence in an amplicon that forms a duplex with one of the amplification primers. In order to design recovery tag binding compounds for use in the aforementioned embodiments, sequence information about a portion of the newly generated sequence must either be known or conjectured. Non-recovery tag based multiplex methods are of particular interest because they permit primers with "universal" template-annealing sequences to be used in the multiplexed sequencing and nucleic acid amplification methods of the invention. The term "universal" is used to indicate that a given template-annealing region of a primer may used with a wide range of templates because the region of the template that the primer anneals to is common to multiple templates.

The present invention provides numerous features that are advantageous when compared to earlier methods of polynucleotide analysis. A significant advantageous aspect of the invention is that increased amounts of sequence information may be obtained from the same or similar amounts of reagents, thereby significantly lowering the costs associated with producing a given unit of sequence information. Another significant aspect is that multiple sequencing ladders may be formed simultaneously in the same reaction vessel. By simultaneously generating a plurality of sequencing ladders in the same reaction vessel, the number of sample handling manipulations is reduced. The invention also reduces the number or manipulations required for other primer extension reactions. Reducing the number of sample manipulations increases the speed with which sequence ladders can be generated and reduces the opportunities for sample handling errors. Other aspects of the invention that make it superior to other multiplex sequencing methods, e.g., the method of Church et al. (U.S. Pat. No. 5,149,625), include the absence of a need for a membrane transfer (blotting) step and the absence of a need for subcloning the polynucleotides for sequencing into special vectors. Other advantages of the invention are that sequencing ladders, amplicons (polynucleotide amplification products), or other primer extension products may be purified, separated, or concentrated with a minimal amount of manipulations.

The degree of reduction in reagent consumption achieved by the methods of the invention is determined, in large part, by the degree of multiplexing. For example, a sequencing reaction that has been multiplexed two-fold, i.e., two sequencing ladders are generated simultaneously in a single reaction vessel, may reduce the requirement of some sequencing reagents up to two-fold. Similarly, a sequencing reaction that has been multiplexed eight-fold, i.e., eight sequencing ladders are generated simultaneously in a single reaction vessel, may reduce the requirements for some reagents up to eight-fold. Thus the invention exploits the "excess" polynucleotide synthetic potential in a single sequence ladder generation reaction.

While particular embodiments of the invention are described herein, it will be apparent to those skilled in the art that alternatives, modifications and variations can be made without departing from the scope of the invention.

The invention claimed is:

1. A method for isolating one or more different-sequence polynucleotides from a mixture, the method comprising:
   (a) flowing the mixture through a flow path containing a plurality of solid supports which are located in series in the flow path, such that the mixture flows serially through each of the plurality of solid supports, each support having bound thereto a sequence-specific capture agent complementary to a different-sequence polynucleotide, under conditions effective to specifically bind different-sequence polynucleotides to corresponding sequence-specific capture agents on one or more of the supports,
   (b) after step (a), releasing bound polynucleotides from a selected support by altering a physical property of that support while leaving unaltered the same physical property of at least one other of the supports, wherein the physical property is temperature, and wherein said releasing is accomplished by heating a first solid support; and
   (c) eluting the released polynucleotides through the flow path such that the eluted polynucleotides can be isolated in separated form.

2. The method of claim 1, wherein said altering further comprises selectively heating a second solid support to release bound polynucleotides therefrom, to allow preferential elution of the polynucleotides released from the second solid support.

3. The method of claim 2, wherein heating of the first and second supports is performed simultaneously, and the polynucleotides released thereby are eluted in separate form, without mixing with each other.

4. The method of claim 1, wherein (i) the polynucleotide mixture comprises a plurality of different polynucleotide populations, each different polynucleotide population comprising a plurality of different polynucleotides that contain a distinct sequence associated with that population, and (ii) different sequence-specific capture agents on the different solid supports are complementary to different polynucleotide populations in the mixture.

5. The method of claim 1, wherein the polynucleotide mixture comprises a plurality of sequencing ladders.

6. The method of claim 1, wherein the polynucleotide mixture comprises a plurality of PCR products.

7. The method of claim 1, wherein the polynucleotide mixture comprises a plurality of ligation products.

8. The method of claim 1, wherein the different-sequence polynucleotides in the mixture include recovery tags for which the capture agents are complementary.

9. The method of claim 1, wherein all of the solid supports in the flow path are located sequentially in the flow path.

10. The method of claim 1, wherein all of the mixture flows through every one of the solid supports as the mixture proceeds down the flow path.

11. The method of claim 1, wherein the solid support has an external surface and the flow path is defined by a structure having an internal surface, and wherein the external surface of the solid support abuts the internal surface of the flow path so that the mixture flows through the solid support in order to proceed down the flow path.

12. The method of claim 1, wherein the solid support has an external surface and the flow path is defined by a structure having an internal surface, wherein the external surface of the solid support is immediately surrounded by the internal surface of the structure defining the flow path.

13. The method of claim 1, wherein the solid support has an external surface and the flow path is defined by a structure having an internal surface, wherein the structure defining the flow path is a cylindrical tube made of heat-shrinkable plastic, and wherein the heat-shrinkable plastic immediately surrounds the external surface of the solid support.

14. The method of claim 1, wherein the flow path is defined by a column.

15. The method of claim 14, wherein the column is a cylindrical column.

16. The method of claim 15, wherein the solid support is a cylindrically shaped frit.

17. The method of claim 16, wherein an external surface of the cylindrically shape frit is immediately surrounded by an internal surface of the column so that all of the mixture flows through the solid support in order to proceed down the flow path.

18. The method of claim 1, wherein the heating of the solid support is achieved via a heating element that enwraps the solid support.

* * * * *